United States Patent [19]
Gugel et al.

[11] Patent Number: 5,836,766
[45] Date of Patent: Nov. 17, 1998

[54] MEDICAL OR DENTAL HANDPIECE

[75] Inventors: Bernd Gugel, Ulm-Einsingen; Bernhard Kuhn, Schemmerhofen, both of Germany

[73] Assignee: Kaltenbach & Voigt GmbH & Co., Biberach, Germany

[21] Appl. No.: 899,098

[22] Filed: Jul. 24, 1997

[30] Foreign Application Priority Data

Jul. 24, 1996 [DE] Germany ................ 196 29 902.0

[51] Int. Cl.$^6$ ..................................... A61C 1/14
[52] U.S. Cl. ........................... 433/127; 415/904
[58] Field of Search ............ 433/126, 127 OR; 415/904

[56] References Cited

U.S. PATENT DOCUMENTS

| | | | |
|---|---|---|---|
| 4,773,856 | 9/1988 | Mosimann | 433/127 |
| 4,874,314 | 10/1989 | Fleer et al. | 433/127 |
| 4,966,552 | 10/1990 | Gonser | 433/132 |
| 5,022,857 | 6/1991 | Matsutani et al. | 433/85 |
| 5,312,252 | 5/1994 | Abbott | 433/132 |

FOREIGN PATENT DOCUMENTS

| | | |
|---|---|---|
| 0 245 692 | 8/1991 | European Pat. Off. . |
| 3442386 | 6/1985 | Germany . |
| 89 13 626.8 | 5/1991 | Germany . |

Primary Examiner—John J. Wilson
Attorney, Agent, or Firm—Scully, Scott, Murphy & Presser

[57] ABSTRACT

A handpiece having a releasable retaining device for a tool having a shaft about which the tool rotates. The handpiece has a housing and a drive sleeve rotatably mounted in the housing. The drive sleeve has a hollow cylindrical insertion hole into which the shaft of the tool is placed. A drive means is provided for rotation of the drive sleeve. First and/or second releasable couplings are provided for rotatably and/or axially connecting the shaft to the drive sleeve. The releasable couplings have either a coupling slider or pressure member which is displaceable between coupling and decoupling positions. An actuating device is provided for displacing the coupling slider or pressure member into their decoupling position. In one embodiment the coupling slider is made of a ceramic material and fabricated into its final form by means of a single fabrication process without after treatment. In another embodiment the coupling slider is made from a ceramic material, and a ring-shaped spring (urging the coupling slider into its coupling position) has ends separated by a distance. The coupling slider has two peripheral grooves on a side opposite a free end of the coupling slider, in which grooves the ends of the ring-shaped spring are disposed. In a third embodiment, the pressure member is fabricated from a ceramic material and has a color mark on a visible surface formed by coloring the ceramic material.

22 Claims, 4 Drawing Sheets

MEDICAL OR DENTAL HANDPIECE

BACKGROUND OF THE INVENTION

1. Field of the Invention

The invention relates to a handpiece in accordance with the preamble of claim 1 or claim 2.

2. Discussion of the Prior Art

A handpiece of this kind is described in DE 34 42 386 A1. With this known configuration the releasable coupling has, for axial connection of the tool shaft with the drive sleeve, a slider (FIG. 1) arranged on on one side of the shaft, or two sliders (FIG. 2) arranged on the two sides of the shaft. With the configuration according to FIG. 1 the slider is displaceable radially, in a radial guide groove of the drive sleeve, between a radially inwardly lying coupling position and a radially outwardly lying release position, and is elastically urged by means of a spring force towards the coupling position. For displacement of the coupling slider into its release position a pressure member is axially displaceable on the side of the handpiece away from the tool, which pressure member upon its inwardly directed displacement meets, with a conical inclined surface, a corresponding inclined surface on the coupling slider and thereby forces the coupling slider into its release position. The coupling slider is a component which in operation rotates with the drive sleeve, whilst the pressure member does not normally take part in this rotation.

With this coupling for axial connection of the tool shaft with the drive sleeve, there can arise in operation considerable frictional wear and tear between coupling slider and pressure member, e.g. when during rotation of the drive sleeve the pressure member is pressed against the coupling slider or sliders and thus a stationary surface on the pressure member meets a rotating surface on the coupling slider. As a result, there arises friction and wear at the coupling surfaces and as a consequence thereof the coupling surfaces are worn away, which leads to damage of the coupling and to failure of the handpiece.

A head housing of a dental handpiece having a similar releasable coupling for axial connection of the shaft with the drive sleeve is described in DE GM 89 13 626.

It is conventional to manufacture the coupling slider or sliders of metal such as steel.

It is also to be emphasized that in particular in the case of such a handpiece for dental purposes, the tool can be driven with a high speed of rotation. For different machining procedures, speeds of rotation of 40,000 rpm and even much higher are usual.

A further problem with such a handpiece lies in that upon rotation a considerable centrifugal force acts on the coupling slider, which tends to draw it into the de-coupling position. Thus, a considerable spring force is needed for the elastic biasing of the coupling slider into the coupling position. This is problematic, because thereby an automatic displacement of the coupling slider into its release position upon the insertion of the tool shaft into the drive sleeve is made more difficult.

SUMMARY OF THE INVENTION

The object of the present invention is to so configure a handpiece or a coupling slider that, whilst ensuring that wear is slight, an easier automatic opening of the coupling upon insertion of the tool shaft into the drive sleeve is possible.

This object is achieved by means of the features of claim 1.

With the configuration in accordance with the invention, the coupling slider is at least in part of a ceramic material, whereby it may at least be partially coated with or may be partially or completely of the ceramic material. By these means, not only is the coupling slider lighter but also more resistant to wear. Due to its small moment of inertia it needs a lesser spring force for elastically urging it into the coupling position. As a consequence, this spring force can be made less than is the case with the known configuration. From this it follows that upon insertion of the tool shaft into the drive sleeve, the coupling slider can be displaced into its release position with a lesser pushing force. With the configuration in accordance with the invention, the tool can be coupled with the drive sleeve more easily and in a more readily manipulable manner. Thereby, the tool is also acted upon by lesser forces, which is of advantage in particular in the case of small or thin tools, since the danger of over-loading or bending of the tool upon coupling is substantially reduced.

Further, the lesser density of the coupling slider in accordance with the present invention leads to lesser moment of inertia and to lesser vibrations in operation. From this there follows also a lesser level of running noise in operation.

Because of the reduced frictional forces, upon actuation of the actuating device, the circumferential forces are significantly reduced and thus also the danger that the coupling slider may by drawn out of its coupling position.

A further advantage consists in that, due to the lesser wear, lesser wear residues (from abrasion) arise in the housing, which is likewise to be desired.

In tests it has been found that the advantages which can be achieved by means of the invention are also achieved when he component or components co-operating with the coupling slider are of metal, in particular of steel, or are likewise of ceramic material. It is thus apparent that the combination of the materials ceramic/metal, in particular steel, or ceramic/ceramic is advantageous.

The invention is advantageous not only with such handpieces in which the coupling slider is a component which rotates with the drive sleeve, but also with such handpieces in which the coupling slider is displaceably mounted in a guide of a housing and for this reason does not take part in the rotation of the drive sleeve and therefore stands in constant sliding contact with the shaft of the tool during rotation.

The above-described advantages also apply to the configuration in accordance with claim 2, in accordance with which the pressure member is of ceramic material or is correspondingly coated.

The invention also relates to a coupling slider, and/or a pressure member, in each case as individual component for a handpiece, which coupling slider or pressure member is formed in accordance with the invention.

Within the scope of the invention, the actuating device may have a pressure member which can be pushed into the housing of the handpiece preferably co-axially and against a spring, and upon pushing-in displaces the coupling slider into its de-coupling position. Thereby, the pressure member can, by means of an inclined or conical section shaped actuating surface strike against a corresponding inclined or conical section shaped actuating surface on the coupling slider. The inclined or conical section shaped actuating surface can be arranged on a web standing up from the coupling slider towards the pressure member.

The return spring for the coupling slider may surround the slider in a ring shape or C-shape, preferably in common with a section of the drive sleeve confronting the coupling slider, whereby the spring can surround the coupling slider and the drive sleeve in a ring shape. Thereby, it is advantageous if the coupling slider has in its preferably cylindrical section shaped outer surface a circumferential groove for receiving the spring, whereby preferably the circumferential groove may continue as a circumferential groove in the outer surface of the drive sleeve. Two circumferential groove sections can be provided on the coupling slider which at their ends towards one another have a spacing from one another, whereby the spring has a C-shaped form, preferably in the manner of a clasp, and the spacing of the spring ends is approximately adapted to the spacing of the groove sections.

The coupling part can be manufactured in a simple and economical manner in a molding tool, whereby the flowable starting material of the coupling slider is transported into the molding tool by means of a feed line, whereby there forms at the mouth of the feed line a so-called initial injection region, which may not be of exact shaping, e.g. because of a closure of the mold chamber after the introduction of the material or because of a breaking off of the hardened excess material in the initial injection region. It is advantageous when the coupling slider has a preferably elongate initial injection region which is arranged on a region of the outer surface particularly an inwardly off-set region of the outer surface—preferably next to the circumferential groove, in particular in the region of an axially projecting web.

It is advantageous if the pressure member has a mushroom-head shaped form having an actuating extension projecting into the housing of the handpiece.

It is further advantageous if the pressure member has a marking on its visible surface which indicates a particular function of the handpiece. The marking is preferably colored or constituted by a color, having in particular the colors red, blue, green and/or yellow. The color of the marking may be arranged only on a partial region, e.g. an indicator position, of the visible surface of the pressure member, or arranged over the entire surface. Further, it is advantageous to form the marking by means of a coloring of the ceramic material at the surface or to color the ceramic material as a whole with the associated color.

The sub-claims contain features which make superfluous an aftertreatment of the coupling slider, improve the coupling of the tool both with regard to its being carried along in rotation and also its axial coupling, further reduce frictional defects, extend life-time, are of simple and economically manufacturable configuration, and make possible an indication of the kind of handpiece involved.

BRIEF DESCRIPTION OF THE DRAWINGS

Below, the invention and further attainable advantages are described in more detail with reference to preferred exemplary embodiments and with reference to the drawings, which show.

DETAILED DESCRIPTION OF THE INVENTION

Figure 1:
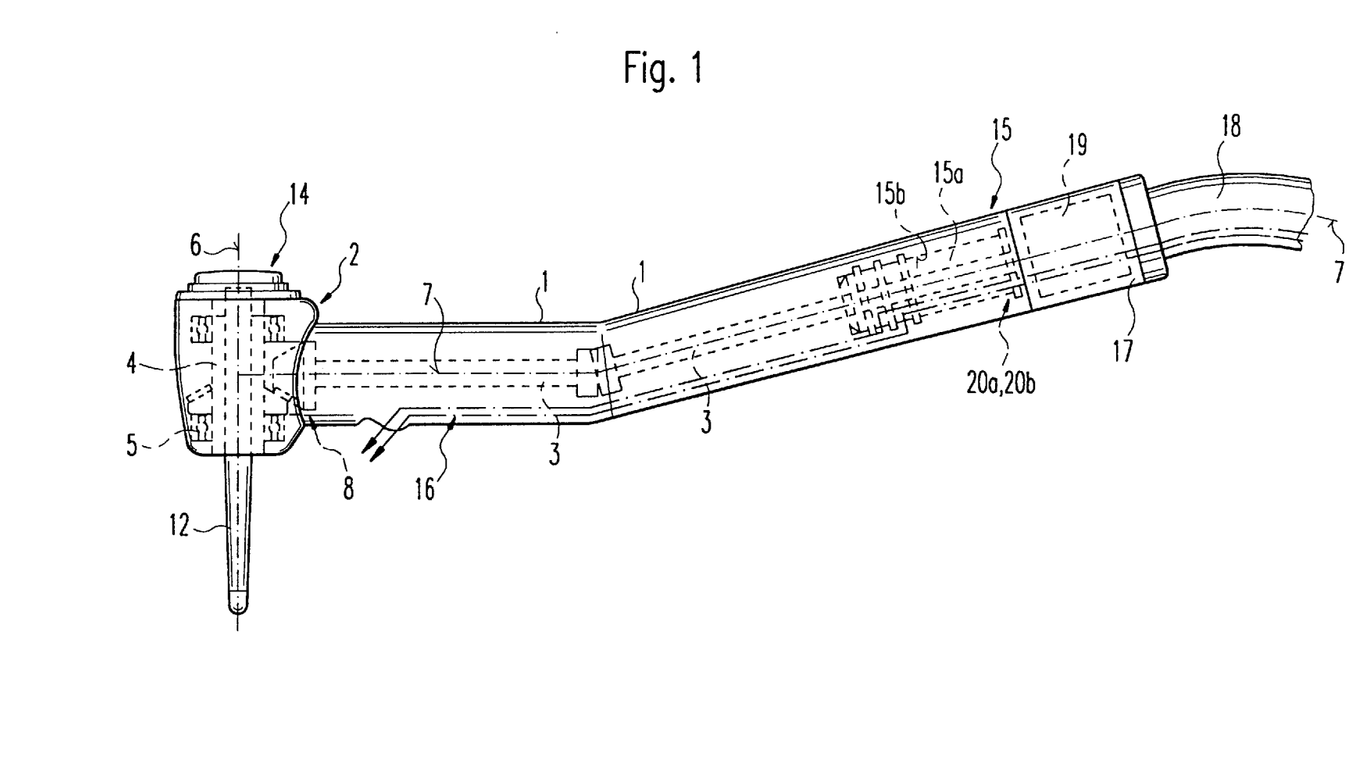
FIG. 1 a handpiece in accordance with the invention, in a side view.
Figure 2:
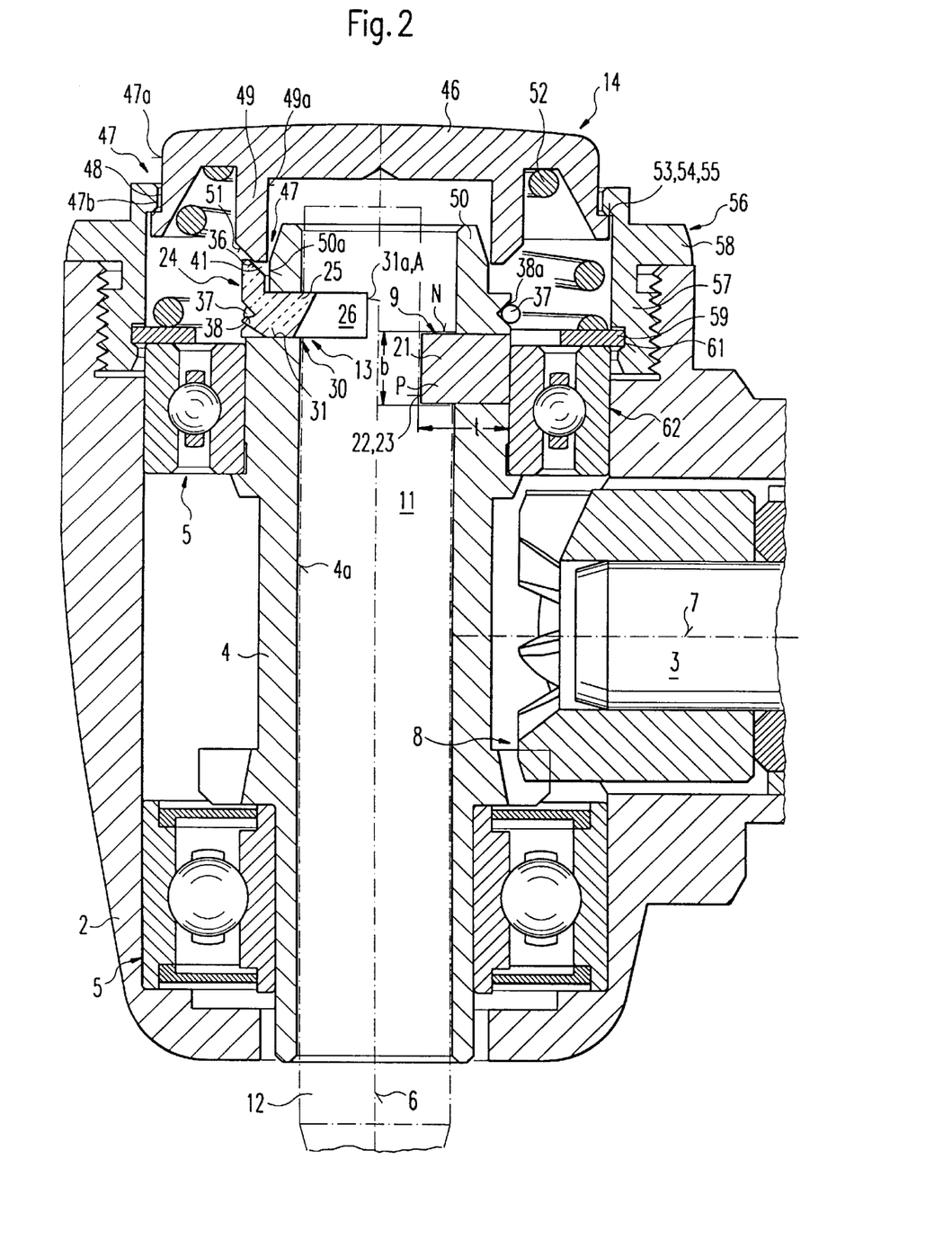
FIG. 2 the head of the handpiece, in vertical section.

Referring now to FIGS. 1 and 2, the main parts of the handpiece concerned are a grip sleeve 1 having a head housing 2 at its forward end, a drive shaft section 3, which is rotatably mounted in the grip sleeve 1, a drive sleeve 4 which is mounted in the head housing 2 to be rotatable by means of rotation bearings 5 about an axis of rotation 6, whereby the axis of rotation 6 preferably extends at right angles to the longitudinal middle axis 7 of the grip sleeve 1, a drive connection between the drive shaft section 3 and the drive sleeve 4, here in the form of an angled transmission 8 with corresponding bevelled gears, a first coupling 9, for providing a connection for carrying along in rotation a shaft 11 of a rotating tool 12 which can be inserted from the outside into the drive sleeve 4, the connection being releasable, a second coupling 13 for releasable axial connection of the shaft 11 with the drive sleeve 4 and an actuating device 14 for releasing the coupling 13 for the purpose of removing the tool 12 from the handpiece.

The grip sleeve 1 can be connected with a connector piece 17 of a flexible supply line 18 by means of a plug-in connection 15 having a coupling pin 15a and a coupling recess 15b which receives the coupling pin, the other end of the flexible supply line being connected with a supply means (not shown) for supplying the handpiece with necessary media, such as e.g. electrical drive energy, blast air, water and/or spray. For this purpose, there serves so-called media lines 16 which may extend longitudinally through the supply line 18 and the plug-in connection 15, as is known per se. The media lines for water and/or air and light end at or in the vicinity of the head housing 2 whereby their exit openings are directed towards the treatment site located at the tip of the tool 12.

The handpiece may be a so-called turbine, with which a drive line carrying compressed air extends, in the above-described sense, up to a drive turbine arranged in the head housing 2. With such a configuration the drive shaft section 3, which in the region of the plug-in connection 15 can be connected by means of a drive element having or being connected with an electric drive motor 19, can be omitted. The drive motor 19 is arranged, in a manner known per se, in the connector piece 17.

Further, it is advantageous to configure the plug-in connection 15 as a plug-in/rotatable connection, so that the handpiece is rotatable relative to the connector part 17, around the longitudinal middle axis 7, whereby the passage of the media lines through the plug-in/rotatable connection is so effected that the passage of the media is ensured in any rotational position. For the media air and/or water there are formed channels which approximately radially cross the cylindrical separation joint between the coupling pin 15a and the coupling recess 15b, which channels stand in connection with respective ring grooves in the region of the joint and are sealed off by means of axially spaced sealing rings. A means preventing unintended release of the plug-in connection 15 is formed by means of a spring element 20a and a recess 20b receiving the element, in the region of the joint, as is known per se.

The first coupling 9 is formed by means of an inner projection 21 in the drive sleeve 4 having a secantial coupling surface 22 which bears against the likewise secantial coupling surface 23 of the shaft, with slight play for movement, whereby the coupling surface 22 is formed by a recess or flattening of the shaft 11 which runs out at the end.

The internal projection 21 is formed by means of a circular section shaped coupling part, which is placed as matching piece in a secantial groove N, which has a corresponding width b and depth t. As can be clearly seen from FIG. 2, the groove N opens out at the outer surface of the drive sleeve, whereby it is arranged at such a height the it is at least partially covered over by the inner ring of the associated rotational bearing 5, which is formed as a roller bearing. By these means, the matching piece P is held in the groove N in a positively locked manner.

The second coupling 13, for axially effective connection of the shaft 11 with the drive sleeve 4, is formed by means of a coupling slider 24, which is radially displaceably mounted, with slight play for movement, in a radial guide slit of the drive sleeve 4, and which has a coupling nose 25 at its radially inward end, and by a coupling recess 26 in the shaft 11 which receives the coupling nose.

Figure 3:
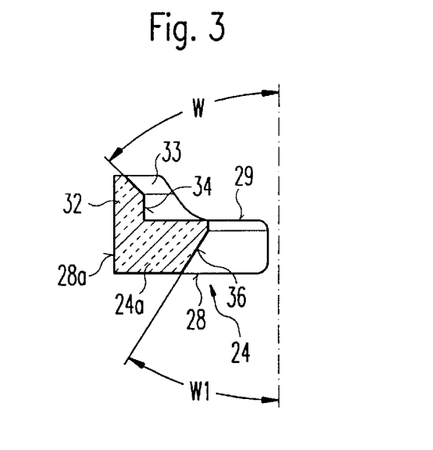
FIG. 3 a coupling slider of the handpiece, in vertical section.
Figure 4:
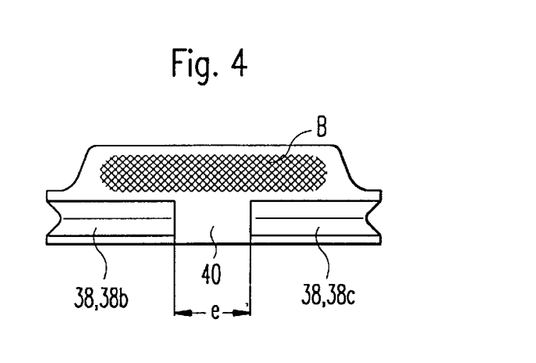
FIG. 4 the coupling slider in a side view from the left.
Figure 5:
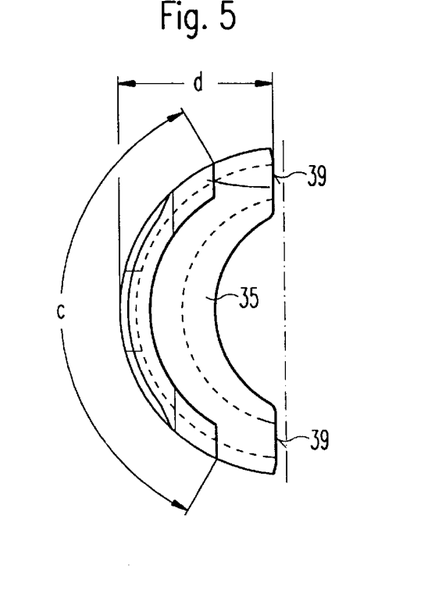
FIG. 5 the coupling slider in a view from above.
Figure 6:
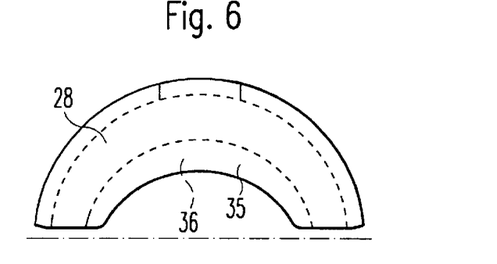
FIG. 6 the coupling slider in a view from below.

The coupling slider 24, illustrated in FIGS. 3 to 5 as an individual part, is when viewed from above of semi-circular shape or of crescent shape, whereby its outer surface is curved in the shape of a cylinder section. The coupling slider 24 consists of two sections connected with one another in one piece, namely a semi-circular shaped slider section 24a having upper and lower surfaces 28, 29 parallel to one another, with which the slider sits with slight play for movement in a radial guide slit 31 in the drive sleeve 4 and is radially displaceable therein. The thus formed radial guide is designated by 30. From the upper surface 29 of the slider section 24a there extends upwardly at the outer edge a cylinder section shape curved web 32, which extends over the entire peripheral section of the coupling slider 24 or only over a part c of the periphery, and has at its upper inner edge a conical section shaped cone surface 33, which includes an upwardly divergent angle W of approximately 45° with the vertical. Preferably, there is arranged below the inner edge of the cone surface 33 another cylindrical section shaped step surface 34 which extends up to the upper surface 29 of the slider section 24a.

The coupling nose 25 is formed on the radially inward side of the slider section 24a, whereby it is formed by means of a circular arc section shaped, or somewhat more widely curved, nose arch 35 running in the peripheral direction, which below has an engagement incline in the form of a conical section shaped cone surface 36. For its stabilization, the nose tip, here the circular section shaped nose arch tip, is preferably blunted by a cylindrical section shaped ring section surface. The downwardly divergent acute angle W1 of the cone surface 36 includes an angle W1 of about 33° with the vertical. The shaft 11 of the tool 12 preferably has at the peripheral edge of its free end an adaptation of corresponding angle or a rounding.

The coupling slider 24 is displaceable between a coupling position illustrated in FIG. 2, in which its inwards movement is limited by means of a stop A and in which coupling nose 25 extends into the hollow cylindrical insertion hole 4a of the drive sleeve 4, and a de-coupling or release position which is outwardly displaced relative thereto, in which de-coupling position the coupling nose 25 does not extend into the insertion hole 4a. The arrangement is so effected that in the coupling position the shaft 11, inserted into the insertion hole 4a, meets the cone surface 36 and by means of this wedge action the coupling slider 24 is displaced into the release position. For self-acting return of the coupling slider 24 into its coupling position there is provided a spring 37 acting upon the coupling slider radially inwardly which spring is formed in the present configuration by means of a ring-shaped spring or a clasp-shaped spring 37 of spring wire which is in section for example round, which wire sits in a circumferential groove 38 in the outer surface 28 for axial securing thereof. Preferably the drive sleeve 4 also has, in the same transverse plane, such a circumferential groove 38a in which the ring-shaped spring 37 sits. Upon displacement of the coupling slider 24 into its release position, the spring 37 is elastically opened, which is made possible by its clasp-shape or C-shape. By means of the springy elastic contraction of the spring 37, the coupling piece 24 is self-actingly displaced into its coupling position. In this position, the spring 37 still exercises a pre-tensioning on the coupling piece 24.

In order to ensure that in the release position the ends of the nose arch 35 also clear the insertion hole 4a, the concave curvature of the nose arch 35 is—seen from above—greater than a corresponding cylinder section shape curvature or is formed with a run-out flank forming a corresponding enlargement, so that the nose arch ends are also, in the release position, located outside of the insertion hole 4a.

With the present configuration the base 31a of the guide slit 31 is arranged diametrically or relative thereto somewhat outwardly radially offset. The radial dimension d of the coupling slider 24 is of corresponding size.

The stop A, limiting the push-in movement of the coupling slider 24a, may be formed between the radially inward bounding surfaces 39 of the coupling slider 24 and the base 31a of the guide slit 31, or between the step surface 34 and the outer surface of the drive sleeve 4. In the present configuration, the outer surface 28 of the coupling slider 24 is approximately in axial alignment with the outer surface of the drive sleeve 4 in the region concerned, whereby there is provided for the web 33 a lateral or concentric recess 41, in particular a coaxial tapering on the drive sleeve 4.

With the present configuration there are provided two groove sections 38b, 38c in the outer surface 28 of the coupling slider 24, which groove sections have—in the side view according to FIG. 4—a spacing e from one another, whereby a web 40 is formed. The ends of the ring-shaped spring 37 have a corresponding spacing e, taking into consideration a play for movement, whereby the installed spring 37 is located with its free ends to the two sides of this web and thereby is secured against turning in the circumferential direction.

The actuating device 14 is provided for releasing the coupling 13, which actuating device is arranged on the side of the head housing 2 away from the tool 12, or is accessible from that side. With the present configuration, the actuating device 14 has a pressure member 46 which is manually displaceable in a guide 47 axially between an inwardly displaced operating position and an outwardly displaced stand-by position.

With the present configuration, the pressure member 46 is a round cap of the head housing 2 which is accessible by means of a preferably round opening 48 of the head housing 2 or penetrates through the opening to the outside and in particular projects beyond the head housing 2 outwardly and thereby closes off the opening 48 with a play for movement ensuring the necessary guiding.

At its inner side, the pressure member 46 has a cylindrical or preferably hollow cylindrical actuating extension 49 which at its free outer edge has an outer cone surface 51 having an angle corresponding to the angle W.

The pressure member 46 is pre-tensioned by means of a spring 52 into its stand-by position, in which its outwardly directed movement is limited by a stop 53 which in the present configuration is formed by means of an inner annular shoulder 54, on which there bears an outer annular shoulder 55 on the pressure member 46 under the pressure of the spring 52 which is preferably provided as a compression spring. The inner end of the compression spring 52 is supported on a shoulder surface of the head housing 2. In the present configuration the pressure member 46 is arranged in an annular insertion piece, in particular screw part 56, which, with a sleeve section 57 having an exterior thread, is screwed into a corresponding internal thread of the head housing 2. Preferably, the insertion piece has a flange 58 which abuts on the upper side of the head housing 2.

The coaxial guide 47 for the pressure member 46 can be realised in many forms. On the one hand, the guide 47 can be formed by means of the outer surface 47*a* of the pressure member 46 and the inner surface 47*b* of the housing 2 or, here, of the screw part 56. On the other hand, there may be provided additionally, or—if appropriate—exclusively, a coaxial guide 47*a* between the cylindrical inner surface 49*a* of the actuating extension 49 and the cylindrical outer surface 50*a* of the facing end region of the drive sleeve 4. No rotational movement takes place in the guide 47, since although the pressure member 46 may be rotatable it does not in normal operation rotate. However, guiding takes place in the guide 47*a* when the pressure member 46 is pushed in and the drive sleeve 4 rotates, e.g. is running down to a stop. This guide 47*a* can thus, in the pushed-in position of the pressure member 46, exercise a slight braking force on the drive sleeve 4 as it runs down to a stop, this within the range of a guide resistance which has the effect of a braking force on the drive sleeve 4.

The internal counter-bearing for the compression spring 52 is formed by means of the spring ring 59 which is placed in a corresponding inner ring groove 61 of the sleeve section 57 in its inner end region. With the present configuration the spring ring 59 with the insertion part or screw part 56 positioned in place, forms an upper limit for the outer ring of a roller bearing 62 forming the associated rotational bearing 6. The insertion piece, the spring ring 59, the compression spring 52 and the pressure member 46 thus constitute a constructional unit which can be pre-assembled, which by means of placement or screwing in can be installed in a simple manner. In the case of a screw part 56 there are provided in the upper region engagement elements (not shown), e.g. mutually oppositely lying insertion holes for a screwing tool. With spring ring 59 deinstalled, the pressure member 46 can be inserted into the insertion or screw part 56 from below, and thereafter the spring ring 59 can be put in place.

In the stand-by position illustrated in FIG. 2, the outer cone surface 51 has a spacing from the inner cone surface 36 corresponding therewith which is preferably small and may be e.g. 1 mm. For opening the coupling 13, the pressure member 46 is pushed in by finger pressure of the operating hand, whereby the cone surfaces 36, 51 meet one another and the coupling slider 24 is displaced radially outwardly into its release position and the shaft 11 can be drawn out of the insertion hole 4*a*. The coupling of the shaft 11 takes place in a self-acting manner upon insertion into the insertion hole 4*a*, by means of displacement of the coupling slider 24 against the spring force and self-acting latching into the recess 26 in the shaft 11, which may be formed with a segmental shape, e.g. as a secantial groove, or may be formed with a ring shape.

With the configuration according to FIGS. 2 to 6, the coupling slider 24 is a component which rotates with the drive sleeve 4. Thus, when the actuating device 14 is actuated for de-coupling to the coupling 13 during the rotation or during the running down of the drive sleeve 4, there arise frictional forces, in particular between the cone surfaces 36, 51 but also in the guide 30 of the coupling slider 24 and/or in the guide 47 of the pressure member 46, which can lead to a wearing down at the contact or guide surfaces, whereby the functional parts are damaged. In order to avoid this and also to afford the coupling slider 24 and/or the pressure member 46 and the components cooperating therewith with a longer working life, the coupling slider 24 is—at least at its frictional surfaces, e.g. at its cone surface 31 and/or at its under surface 28, and/or its upper surface 29, and/or the pressure member 46 at its outer surface 47*a* and/or at its inner surface 49*a* and/or its cone surface 51—coated with a ceramic material or is manufactured in the regions of the above-mentioned surfaces of ceramic material, or is manufactured as a whole of ceramic material, preferably in one piece. By these means, the slidability of the frictional surfaces is improved, which extends the working life of the components in frictional engagement with one another and reduces the generation of heat. These advantages are independent of whether the frictional surfaces can be lubricated or not. The invention thus leads to a further advantage that the lubrication and care of the frictional surfaces is reduced or is no longer necessary.

In the case of manufacture of the coupling slider as a whole of ceramic material, it can be manufactured as a molded part, as an injected part, or as a cast part or as a stamped part. It has been determined that no aftertreatment is needed after the manufacture of the coupling slider; rather the coupling slider can be manufactured directly in its final form with the above-mentioned manufacturing steps, which leads to a substantial simplification of manufacture and reduces the manufacturing costs.

In tests, a polycrystalline ceramic has proved to be an advantageous ceramic material, in particular with a high degree of purity of, e.g. 99% and more.

When the coupling slider 24 is produced as an injected part, it is advantageous to arrange the initial injection region B, emphasized in FIG. 4 by means of cross-hatching, at the surface 28, in particular in the region of the web 32. In this region an inexactitude of an outer surface, caused by the initial injection, is least disruptive. Thereby, the outer surface in the region of the web 32 maybe slightly radially inwardly offset relative to the remaining outer surface 28, as shown by FIG. 5.

Figure 7:
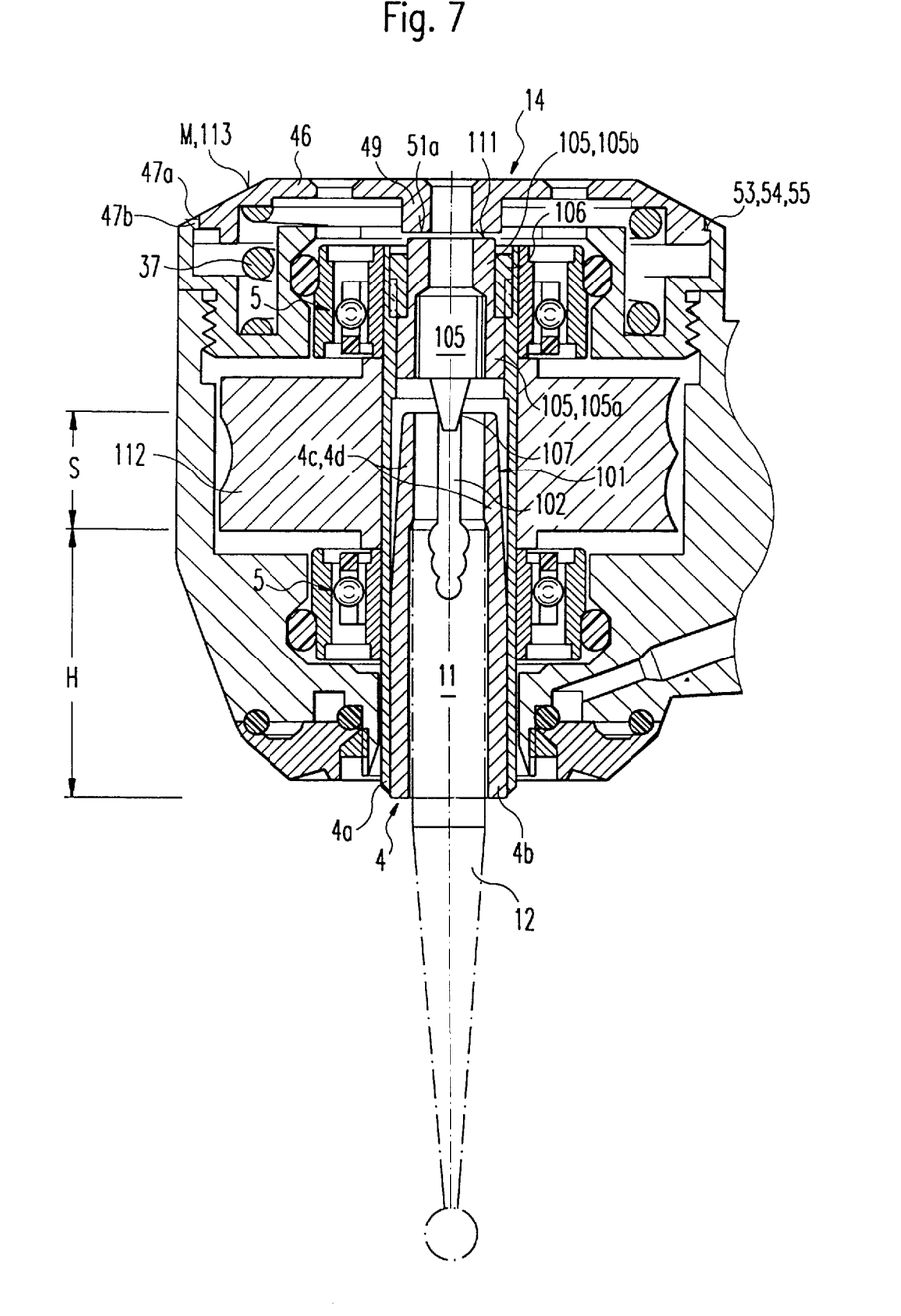
FIG. 7 the head of a handpiece in accordance with the invention in a further modified configuration, in vertical section.

With the configuration according to FIG. 7, in which the same or similar parts are likewise provided with the same reference signs, there is provided between the drive sleeve 4 and the shaft 12 a coupling 101 which is effective through force coupling in the manner of a clamping coupling. This coupling 101 is at the same time effective in the axial direction and also in the peripheral direction. The drive sleeve consists of an outer bearing sleeve 4*a* and a chucking sleeve 4*b*, fixedly emplaced therein, the inward end region of which, or the end region of which away from the tool 12, is outwardly tapered as chucking region.

This coupling 101 is known. It is formed by means of two chucking sleeve segments 4*c*, 4*d* lying diametrically oppositely to one another, which are separated from one another by an axial slit 102 which runs out at the end of the shaft 11 away from the tool 12 and which extends towards the tool head in the chucking region designated with S and also extends in the retention region of the drive sleeve 4 designated by H, and ends in that region. In the chucking region S the inner cross-sectional dimension of the substantially hollow cylindrical chucking sleeve 4*b* is somewhat lesser than in the retention region H. Upon further pushing-in of the shaft 11, from the intermediate position illustrated in FIG. 7, the mounting segments 4c, 4d separated from one another by the slit 102 are consequently spread apart whereby they elastically bend outwardly and bear upon the shaft 11 with pre-tensioning, which ensures chucking. The coupling of the shaft 11 thus is effected self-actingly upon insertion of the same into the chucking sleeve 4b.

For de-coupling, a pressure slider 105 is axially displaceably mounted in the bearing sleeve 4a above the chucking sleeve 4b, which bearing sleeve 4a—at its end towards the chucking sleeve 4b—has two pressure parts 87 lying diametrically oppositely to one another, which engage into the slit 102, as shown in FIG. 7. The pressure slider 105 has a lower, enlarged longitudinal section 105a, which is mounted in the bearing sleeve 4a with play for movement and has an upper longitudinal section 105b which is tapered in diameter. In this ring-shaped hollow chamber there is associated with the axially movably pressure slider 105 a stop member 106—limiting the movement of the pressure slider away from the drive sleeve 4—for establishing a pre-setting of the chucking segments 4c, 4d. The stop member is formed by a setting ring screwed into the upper end of the bearing sleeve 4a.

Above the pressure slider 105, a pressure member 46 is mounted at the upper end of the housing 2 coaxially displaceable in a guide 47, which pressure member can be manually pushed in between its stand-by position illustrated in FIG. 7 and an inwardly displaced actuating position, and can be returned by means of the pressure spring 37 into its stand-by position. The arrangement and function of this pressure member 46 corresponds in substance to the configuration according to FIG. 2, but here the actuating extension 49 presses with a radial end face 51a against the upper radial end face 111 of the pressure slider 105 when the pressure member—forming the housing cover—is pushed in. This leads to an opening of the coupling 101 in that the pressure wedge 107 spreads apart the chucking segments 4c, 4d and thereby the shaft is freed.

As is the case for the exemplary embodiment according to FIG. 2, the pressure member 46 also is coated with a ceramic material in the region of its guide surfaces 47a and/or in the region of its pressure surface 51a. It may also be made of ceramic material in these regions, or preferably may be made as a whole of ceramic material. By these means the above-described advantages are also attained with this exemplary embodiment.

Otherwise, the configuration according to FIG. 7 differs in that the drive sleeve 4 with the associated bearing 5 is mounted in the screw part 56 and there is provided a per se known turbine drive having a turbine wheel 112 arranged on the drive sleeve 4.

As with the coupling sliders 24, the pressure member 46 also can be manufactured simply and economically as a molded part or as an injected part or as a cast part or as a stamped part. Thereby no aftertreatment is needed after its manufacture and it can be produced by the above-mentioned manufacturing steps directly in its final form.

In dental practice it has become usual to designate handpieces which differ with regard to their transmission ratios or other properties, e.g. designs with lighting, with different colors. For step-up gearing a red designation M is applied, for step-down gearing a green designation M, for a 1:1 gearing a blue designation M, for lighting a yellow designation M. With the present configuration, this color designation is applied on the visible outer surface of the pressure member 46, whereby the color designation may be arranged over the entire surface or only on one part of the surface. It is also advantageous to provide the pressure member 46 as a whole with the desired color. This can also be of advantage for technical manufacturing reasons. With the present configuration, the desired color can be mixed into the ceramic material in a simple and economical manner, both when the color is mixed into the entire material of the pressure member 46 and also when only a small part 113, e.g. a small circular area, is to be colored. With reference to the above-described configurations, the colors red, blue, green or yellow can be employed.

The coloring of the material leads to the advantage that the color is not present merely in one layer which can peel off or be worn off, but which because of the coloring is penetratingly colored and is not sensitive to damage or wearing off.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical or dental handpiece having a releasable retaining device for a tool, the tool having a shaft about which the tool rotates, the handpiece comprising:

a housing;

a drive sleeve rotatably mounted in the housing, the drive sleeve having a hollow cylindrical insertion hole into which the shaft of the tool is placed;

a drive means for rotation of the drive sleeve;

a first releasable coupling for rotatably connecting the shaft to the drive sleeve such that the shaft rotates with the drive sleeve about a common axis of rotation;

a second releasable coupling for axially connecting the shaft to the drive sleeve, the second releasable coupling comprising a coupling recess in the shaft, a coupling slider displaceable in a guide transverse to the axis of rotation of the drive sleeve between a coupling position engaging into the coupling recess and a decoupling position releasing the shaft from the handpiece, and a spring urging the coupling slider into its coupling position; and an actuating device for displacing the coupling slider into its decoupling position;

whereby the coupling slider is made of a ceramic material and fabricated into its final form by means of a single fabrication process without after treatment.

2. The handpiece of claim 1, wherein the coupling slider is fabricated in one piece.

3. The handpiece of claim 1, wherein the fabrication process for the fabrication of the coupling slider is selected from a group consisting of molding, injecting, casting, and stamping.

4. The handpiece of claim 1, wherein the coupling slider has upper and lower surfaces parallel to one another.

5. The handpiece of claim 1, wherein the coupling slider is, with regard to the axis of rotation of the drive sleeve, arranged on one side.

6. The handpiece of claim 1, wherein the coupling slider has, viewed along the axis of rotation, a half-ring form.

7. The handpiece of claim 1, wherein the coupling slider has a coupling nose having a nose bridge, wherein the coupling movement of the coupling slider is restricted by a stop in such a position that upon insertion into the drive sleeve the shaft of the tool impacts against the nose bridge and displaces the coupling slider into its decoupling position.

8. The handpiece of claim 1, wherein the actuating device is manually accessible from a side of the housing away from the tool.

9. A medical or dental handpiece having a releasable retaining device for a tool, the tool having a shaft about which the tool rotates, the handpiece comprising:

a housing;

a drive sleeve rotatably mounted in the housing, the drive sleeve having a hollow cylindrical insertion hole into which the shaft of the tool is placed;

a drive means for rotation of the drive sleeve;

a first releasable coupling for rotatably connecting the shaft to the drive sleeve such that the shaft rotates with the drive sleeve about a common axis of rotation;

a second releasable coupling for axially connecting the shaft to the drive sleeve, the second releasable coupling comprising a coupling recess in the shaft, a coupling slider having a surface shell and displaceable in a guide transverse to the axis of rotation of the drive sleeve between a coupling position engaging into the coupling recess and a decoupling position releasing the shaft from the handpiece, and a ring-shaped spring mounted in the surface shell and radially urging the coupling slider into its coupling position; and an actuating device for displacing the coupling slider into its decoupling position;

whereby the coupling slider is fabricated from a ceramic material, the ring-shaped spring further having ends separated by a distance, wherein the coupling-slider has two peripheral grooves on a side opposites a free end of the coupling slider, in which grooves the ends of the ring-shaped spring are disposed.

10. The handpiece of claim 9, wherein the coupling slider is fabricated in one piece.

11. The handpiece of claim 9, wherein the fabrication process for the fabrication of the coupling slider is selected from a group consisting of molding, injecting, casting, and stamping.

12. The handpiece of claim 11, wherein the coupling slider is by means of its fabrication process, produced in a single piece, without after treatment.

13. The handpiece of claim 9, wherein the coupling slider has upper and lower surfaces parallel to one another.

14. The handpiece of claim 9, wherein the coupling slider is, with regard to the axis of rotation of the drive sleeve, arranged on one side.

15. The handpiece of claim 9, wherein the coupling slider has, viewed along the axis of rotation, a half-ring form.

16. The handpiece of claim 9, wherein the coupling slider has a coupling nose having a nose bridge, wherein the coupling movement of the coupling slider is restricted by a stop in such a position that upon insertion into the drive sleeve the shaft of the tool impacts against the nose bridge and displaces the coupling slider into its decoupling position.

17. The handpiece of claim 9, wherein the actuating device is manually accessible from a side of the housing away from the tool.

18. A medical or dental handpiece having a releasable retaining device for a tool, the tool having a shaft about which the tool rotates, the handpiece comprising:

a housing;

a drive sleeve rotatably mounted in the housing, the drive sleeve having a hollow cylindrical insertion hole into which the shaft of the tool is placed;

a drive means for rotation of the drive sleeve;

a releasable coupling for rotatably and axially connecting the shaft to the drive sleeve such that the shaft rotates with the drive sleeve about a common axis of rotation, the releasable coupling being urged into a connecting position by a first spring; and an actuating device having a pressure member mounted on an outer side of the housing facing away from the tool, the actuating device being displaceably guided in an axial guide in the housing between an outer release position and an inner connection position, the actuating device being urged into its release position by a second spring;

whereby the pressure member is made of a ceramic material and has a color mark on a visible surface which is formed by coloring the ceramic material.

19. The handpiece of claim 18, wherein the pressure member is fabricated in one piece.

20. The handpiece of claim 18, wherein the fabrication process for the fabrication of the pressure member is selected from a group consisting of molding, injecting, casting, and stamping.

21. The handpiece of claim 20, wherein the pressure member is by means of its fabrication process, produced in a single piece, without after treatment.

22. The handpiece of claim 18, wherein the actuating device is manually accessible from a side of the housing away from the tool.

* * * * *